United States Patent [19]

Graff et al.

[11] Patent Number: 5,164,921
[45] Date of Patent: Nov. 17, 1992

[54] ELECTRODYNAMIC PERMANENT MAGNET TRANSDUCER

[75] Inventors: Alfred Graff, Essen; Hans-Jürgen Rohde, Duisburg, both of Fed. Rep. of Germany

[73] Assignee: Mannesmann AG, Düsseldorf, Fed. Rep. of Germany

[21] Appl. No.: 703,255

[22] Filed: May 20, 1991

[30] Foreign Application Priority Data

May 21, 1990 [DE] Fed. Rep. of Germany ....... 4016740

[51] Int. Cl.⁵ ...................... G01N 9/24; G01N 29/04
[52] U.S. Cl. ..................................... 367/140; 73/643
[58] Field of Search .................. 324/226; 73/643; 367/140

[56] References Cited

U.S. PATENT DOCUMENTS 4,777,824 10/1988 Alers .................................. 324/226
5,050,703 9/1991 Graff et al. ............................ 73/643

OTHER PUBLICATIONS

B. W. Maxfield, et al., "Evaluating EMAT Designs for Selected Applications", Materials Evaluation Oct. 1987, pp. 1166–1183.

Primary Examiner—J. Woodrow Eldred
Attorney, Agent, or Firm—Nils H. Ljungman and Associates

[57] ABSTRACT

An electrodynamic permanent magnet transducer for the non-destructive testing of workpieces by means of ultrasound. A soft magnetic housing is preferably provided in magnetically conducting contact with a pole surface of the permanent magnet to provide a compact magnetic return path for the magnetic field created by the permanent magnet. A hollow cylindrical body of nonmagnetic material is disposed to contactingly surround the permanent magnet to substantially eliminate magnetic short circuits parallel to the pole axis of the permanent magnet. The provision of two spiral transducer coils allows for the transmission and reception of ultrasound in a single permanent magnet transducer.

17 Claims, 5 Drawing Sheets

ELECTRODYNAMIC PERMANENT MAGNET TRANSDUCER

BACKGROUND OF THE INVENTION

1. Field of the Invention

The present invention relates to an electrodynamic permanent magnet transducer.

2. Background Information

Electrodynamic permanent magnet transducers are generally used for the non-destructive testing of workpieces by means of ultrasound. A survey of the current status of development of such electrodynamic permanent magnet systems appears in *Materials Evaluation* (45), October 1987, pages 1166 ff. In essence, this survey discloses the use of a permanent magnet in combination with a spiral flat coil, wherein the spiral flat coil serves as a transducer coil. Such an embodiment is known as an open magnetic system, that is, a system in which the permanent magnet is oriented with one of its pole surfaces disposed toward a surface of a workpiece to produce magnetic field lines there. As such, the magnetic field lines generally have a magnetic return path through the air.

Essentially, in the transducer coil, located between the permanent magnet and the workpiece surface, high-frequency initial pulses are generated to induce eddy currents in the surface of the workpiece to be inspected. The pulses interact with the imposed static magnetic field and thereby generate ultrasound.

A disadvantage of this known arrangement may be found in that, because only one transducer coil is installed on the side of the permanent magnet transducer to be applied onto the workpiece to be tested, only a transmission or a reception operation can be conducted, but not both simultaneously. Consequently, an arrangement consisting of two separate permanent magnet transducers would generally be necessary to use this known permanent magnet transducer for the simultaneous transmission and reception of ultrasound waves.

Further, it should be noted that, with this known permanent magnet transducer, only a portion of the total available magnetic field can generally be used for the generation of ultrasound because, in the magnetic return path through the air, only insufficiently high field densities can generally be achieved. Also, the electrical connections of this known permanent magnet transducer are generally provided by means of a coaxial cable connection located on a side portion of the housing which projects considerably beyond the peripheral area of the housing. A disadvantage of this arrangement may be found in that such a location of the coaxial cable connection may make handling of the apparatus difficult.

OBJECT OF THE INVENTION

The object of the invention, therefore, is to refine the permanent magnet transducer so that sufficiently high magnetic field densities can be generated, and so that the simultaneous transmission and reception of ultrasound waves may be permitted, whereby the entire apparatus is compact and advantageously suitable for manual testing.

SUMMARY OF THE INVENTION

The object of the invention is achieved with an electrodynamic permanent magnet transducer of the type described above, by means of a combination of characteristic features to be discussed hereinbelow. Additional advantageous configurations of the invention are also disclosed hereinbelow. It should be understood that the electrodynamic permanent magnet transducer of the present invention may be alternatively termed an "electromagnetic transducer" or an "electromagnetic acoustic transducer".

According to the invention, a soft magnetic housing is preferably provided in a magnetically conducting connection between the surface of the workpiece and a pole surface of the permanent magnet, particularly that pole surface which faces away from the workpiece surface. Preferably, by means of the use of the soft magnetic housing, a magnetic return path is formed with the workpiece in a very advantageous and compact manner, thus essentially increasing the efficiency of the ultrasound generation and detection. Essentially, the magnetic field return path is routed via the soft magnetic housing, instead of through the air, directly from the surface of the workpiece back to the pole of the permanent magnet which faces away from the workpiece.

Another embodiment of the invention provides for an arrangement of a hollow cylindrical body, preferably made of nonmagnetic material, located inside the soft magnetic housing. The permanent magnet is then preferably located inside the nonmagnetic cylindrical body so that magnetic short circuits parallel to the pole axis of the permanent magnet are, essentially, advantageously eliminated.

Also, a support body holding the transducer coils is preferably located flush with the housing in the opening of the housing to essentially guarantee that the magnetic field lines of the permanent magnet and the transducer coils can be brought as close as possible to the workpiece surface that is to be tested. At the same time, such an arrangement generally guarantees that the housing is also in contact with the workpiece surface to be tested, without an air gap, in the peripheral region, and can thus form an essentially optimal magnetic return path.

The present application of a second spiral transducer coil advantageously allows for both the transmission and reception of ultrasound in a single permanent magnet transducer. As proposed by the present invention, the installation of a separate connector box on the electrodynamic permanent magnet transducer has the advantage that passive conducting means for the electrical connection to a signal processing unit can be installed in an eccentric recess proposed according to the invention. The fact that the recess is located eccentrically means that coaxial cable connections, according to the invention, can be advantageously located in an almost completely countersunk manner in the electrodynamic permanent magnet transducer. This also has the advantage that the electrodynamic permanent magnet transducer, according to the invention, is generally easier to handle and operate.

In summary, one aspect of the invention resides broadly in an electrodynamic magnet transducer at least for detecting defects in a workpiece, the transducer comprising: an external housing; magnet means disposed within the housing; the magnet means having a first pole and a second pole, the first pole for being disposed substantially toward the workpiece; the magnet means being for producing a magnetic field, the magnetic field for being applied to the workpiece; coil means for inducing current in the workpiece, the coil means being configured for being disposed substantially adjacent the workpiece; the first pole of the magnet means being disposed substantially adjacent the coil means; the second pole of the magnet means being disposed substantially opposite the first pole of the magnet means; magnetic conducting means being in magnetically conducting contact with the second pole of the magnet means; and the magnetic conducting means for being disposed to be in simultaneous magnetically conducting contact with the workpiece and the second pole of the magnet means to direct the magnetic field between the workpiece and the second pole of the magnet means.

Another aspect of the invention resides broadly in an electrodynamic magnet transducer at least for detecting defects in a workpiece, the transducer comprising: an external housing; magnet means disposed within the housing; the magnet means having a first pole and a second pole, the first pole for being disposed substantially toward the workpiece; the magnet means being for producing a magnetic field, the magnetic field for being applied to the workpiece; coil means for inducing current in the workpiece, the coil means being configured for being disposed substantially adjacent the workpiece; the first pole of the magnet means being disposed substantially adjacent the coil means; the second pole of the magnet means being disposed substantially opposite the first pole of the magnet means; the coil means comprising at least two transducer coils; one of the at least two transducer coils being for transmitting sonic pulses; and another of the at least two transducer coils being for receiving sonic pulses.

Yet another aspect of the invention resides broadly in an electrodynamic magnet transducer at least for detecting defects in a workpiece, the transducer comprising: an external housing; magnet means disposed within the housing; the magnet means having a first pole and a second pole, the first pole for being disposed substantially toward the workpiece; the magnet means being for producing a magnetic field, the magnetic field for being applied to the workpiece; coil means for inducing current in the workpiece, the coil means being configured for being disposed substantially adjacent the workpiece; the first pole of the magnet means being disposed substantially adjacent the coil means; the second pole of the magnet means being disposed substantially opposite the first pole of the magnet means; and nonmagnetic means at least partially surrounding the magnet means to substantially eliminate magnetic short circuiting of the static magnetic field.

BRIEF DESCRIPTION OF THE DRAWINGS

The invention is explained in greater detail below, with reference to the accompanying drawings, wherein.

DESCRIPTION OF THE PREFERRED EMBODIMENTS

Figure 1:
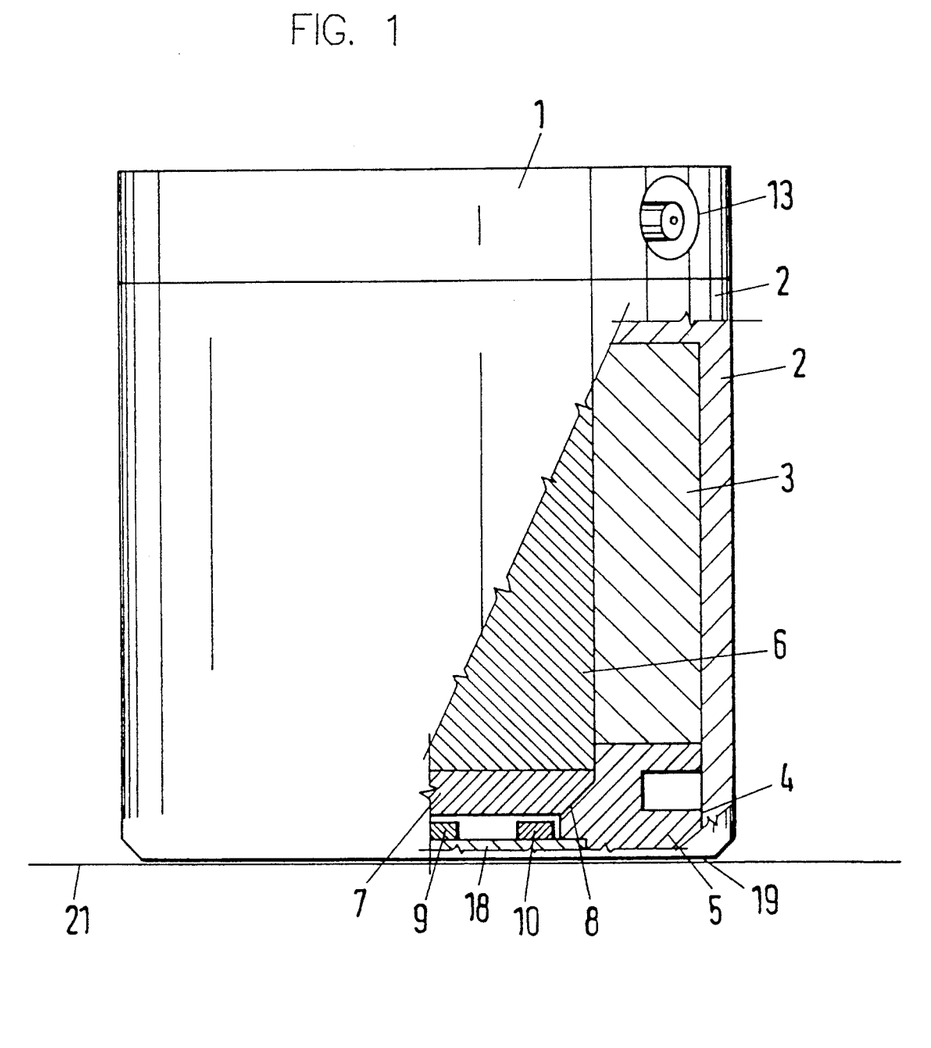
FIG. 1 shows an overall view of the electrodynamic permanent magnet transducer.

The overall view in FIG. 1 illustrates the location of essentially all the individual parts in relation to one another. The connector box 1 is preferably located on the soft magnetic housing 2 and its shape and external dimensions are preferably adapted to be essentially the same as those of the soft magnetic housing 2. The result, then, is an overall cylindrical shape of the permanent magnet transducer. Preferably, inside the soft magnetic housing 2 is a hollow cylindrical body 3 comprising a nonmagnetic material, such as aluminum. The support body 5 is preferably located in an opening 4 provided in the lower part of the permanent magnet transducer and is preferably in flush contact with the external surface of the permanent magnet transducer. A concentrator body 7 may lie flush with a conical portion of a recess 8 of the support body 5 and flush against the pole surface of the permanent magnet 6 facing the workpiece surface. Therefore, the permanent magnet 6 and the concentrator body 7 are located inside the overall arrangement of the permanent magnet transducer. Preferably, two transducer coils 9, 10 are located in a recess provided in an external surface 19 of the support body 5, particularly in the surface to be applied to the workpiece surface. The electrical contacting or connections of the transducer coils 9, 10 are preferably afforded by means of holes leading to the connector box 1 through the support body 5, the cylindrical body 3 and the floor of the housing 2 facing away from the workpiece surface. A substantially countersunk coaxial cable connection is preferably located in a hole 13 in the connector box 1.

Figure 2:
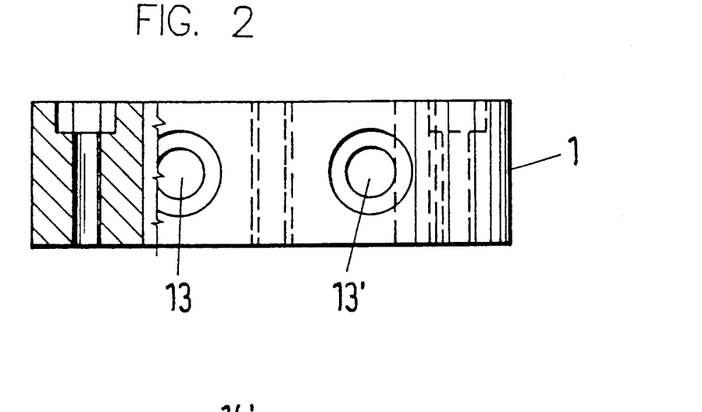
FIGS. 2 and 2a show, respectively, an elevational view and a plan view of the connection box.
Figure 2A:
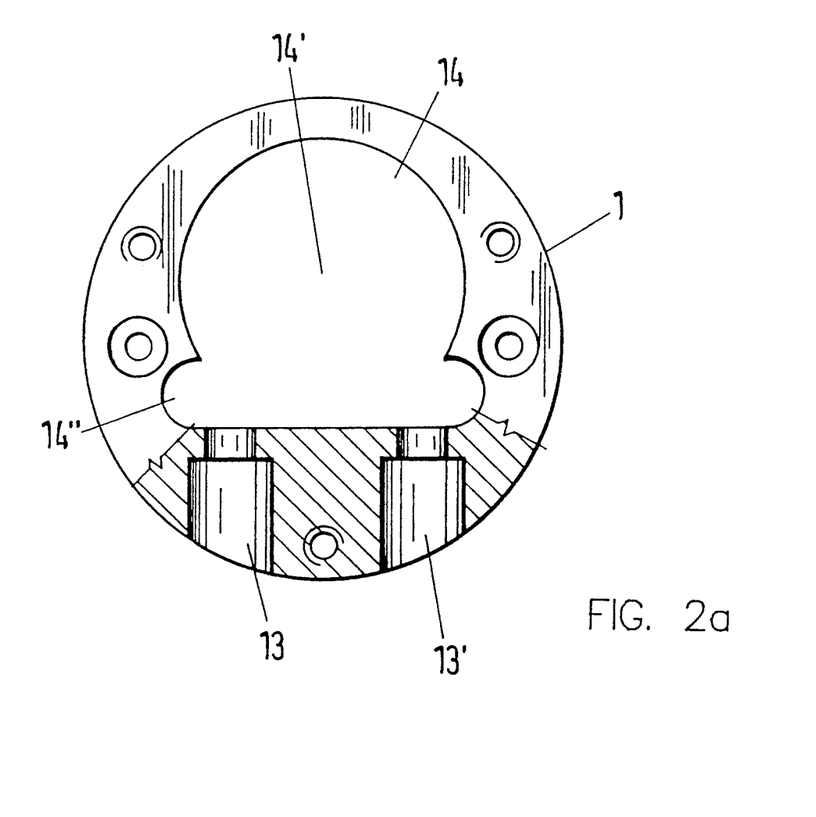

FIG. 2 shows the connector box 1 in a side view and FIG. 2 shows the same in an overhead view. FIGS. 2a shows the location of a recess 14 and a functionally advantageous form thereof. Particularly, the hole or recess 14 in question is preferably an eccentrically located hole 14' with a milled opening 14". Preferably, the general shape of the milled opening is that of an elongated figure in which two substantially equal semicircles, whose concave portions face each other, are connected by two parallel lines, each of which lines originates at an end point of each of the semicircle arcs. Furthermore, this shape of the milled opening 14" is superimposed upon the generally circular shape of the hole 14' such that, as shown in FIG. 2a, the milled opening 14" generally cuts across the hole 14' in the manner of a secant. Holes 13 and 13', provided for holding the coaxial cable connections, are preferably disposed to extend laterally up to the milled opening 14", thus being afforded an entry to the connector box 1 and the eccentric hole 14' thereof. More particularly, the holes 13 and 13' preferably have a longitudinal axis substantially normal to the longitudinal axis of the milled opening 14" and thus, essentially, meet the milled opening 14" at right angles. Passive conducting means, such as cable, lines or ohmic resistances, can be located within the recess 14. The connector box 1 is preferably closable by means of a cover on at least one side.

Figure 3:
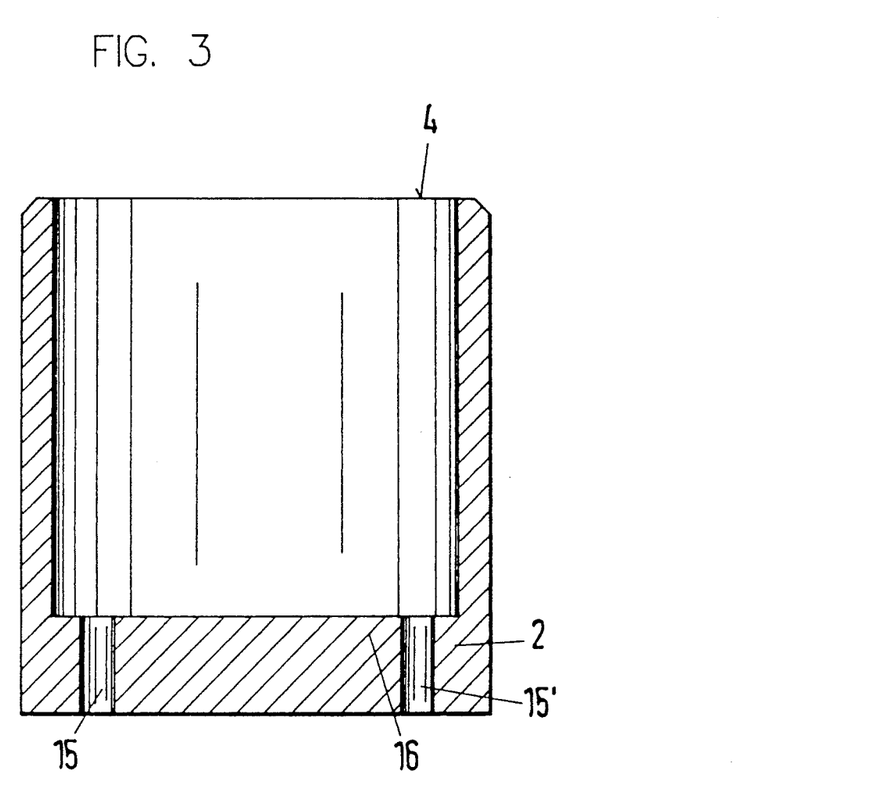
FIGS. 3 and 3a show, respectively, a cutaway elevational view and a plan view of the soft iron housing.
Figure 3A:
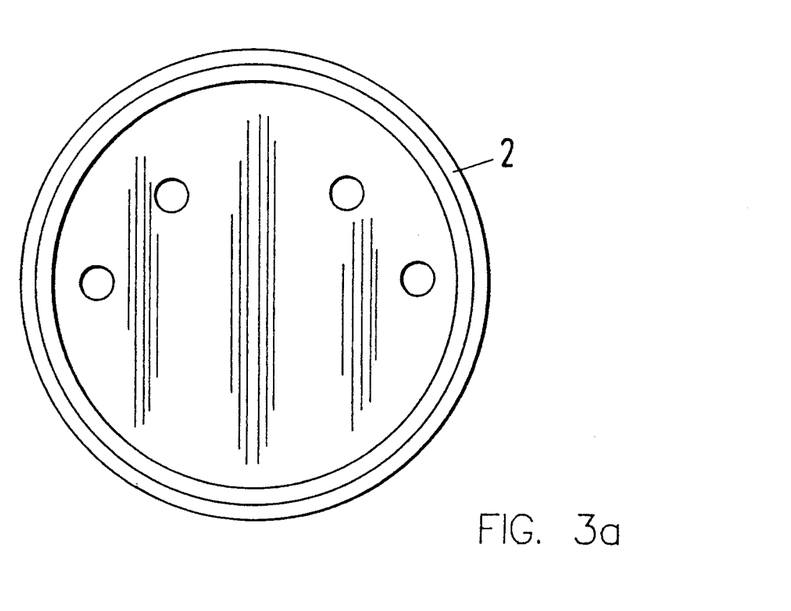

FIGS. 3 and 3a show, respectively, a side view and an overhead view of the soft magnetic housing 2. The opening 4 in the housing 2 is preferably made wide enough so that the diameter of the opening extends over the entire inside diameter of the housing. This type of construction usually guarantees easy installation, and is also generally uncomplicated in terms of fabrication complexity. Preferably, in a closed bottom 16 of the housing 2, there are holes 15, 15' which can be used for the passage of the cable therethrough or for the fastening together of the individual segments of the permanent magnet transducer.

Figure 4:
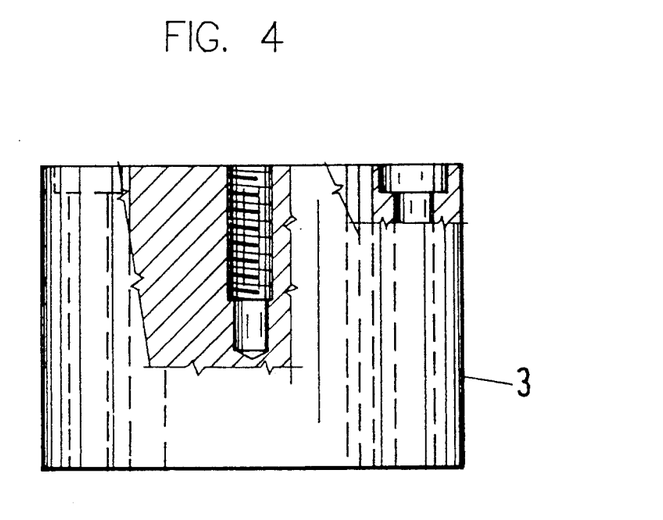
FIGS. 4 and 4a show, respectively, a cutaway elevational view and a plan view of the hollow cylindrical body as the permanent magnet guide.
Figure 4A:
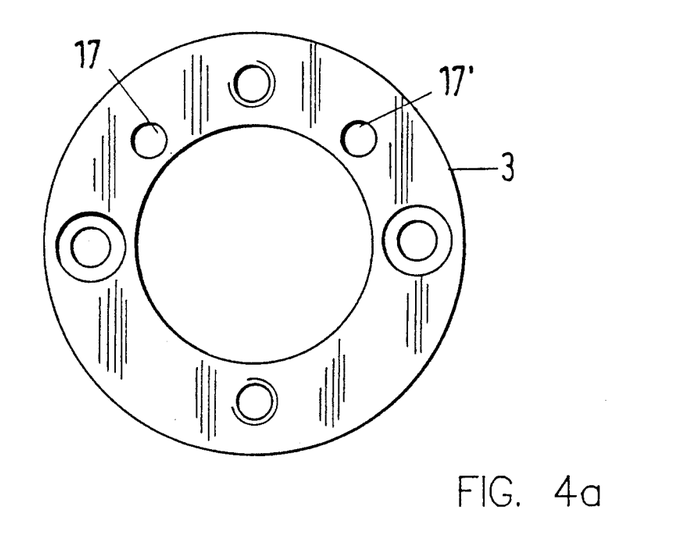

FIGS. 4 and 4a show, respectively, a side view and an overhead view of the hollow cylindrical body 3, whose outside diameter preferably forms a size of fit in relation to the inside diameter of the housing 2. That is, the outside diameter of the hollow cylindrical body 3 is preferably such that the hollow cylindrical body 3 may easily fit within the inside diameter of the housing 2. The holes 17, 17' are preferably offset from one another by an angle of about 90 degrees about the periphery of the cylindrical body 3, and coincide with the holes in the floor of the housing 2. These holes are preferably to be used to hold and guide the electrical connecting cable between the transducer coils 9, 10 and the electrical connector box 1. After assembly, these holes may be plugged with a plastic compound.

Figure 5:
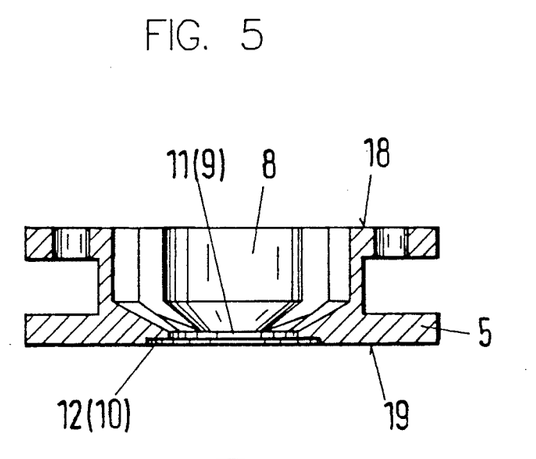
FIGS. 5 and 5a show, respectively, a cutaway elevational view and a plan view of support bodies to hold the transducer coils and the concentrator body.
Figure 5A:
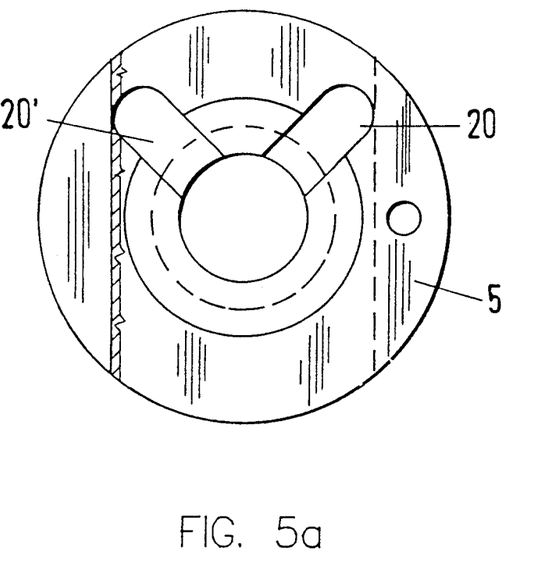

FIGS. 5 and 5a show, respectively, a side view and an overhead view of the support body 5 for holding concentrator body 7 and the transducer coils 9,10. It is highly desirable that concentrator body 7 have dimensions such that, when it is placed within the support body 5, it occupies and substantially fills at least the space of the conical portion of the hole 8. As a result, the permanent magnet can essentially come into direct contact with the concentrator body. On the outer surface 19 of the support body 5 facing the workpiece surface, recesses 11, 12 are visible. The overhead view shows two additional recesses 20, 20', preferably offset by about 90 degrees. Recesses 20, 20' are preferably configured to receive the connection wires for the transducer coils 9, 10. Particularly, in an appropriate positioning, holes 17, 17' and recesses 20, 20' preferably align with each other to permit the wires to also be led to the hollow cylindrical body 3 and the housing 2. Thus, a passage for the connection wires can essentially be formed between the connector box 1 and the transducer coils 9, 10.

FIG. 1 shows the disc 18 with the layout of the transducer coils 9, 10 disposed therein. The disc, in the assembled state, preferably fits into the first recess 12 so that the transducer coils project into the second recess 11 (See FIG. 5). The side of the disc 18 facing the workpiece surface preferably fits flush with the surface 19 of the support body 5.

The overall height of a permanent magnet transducer, such as that disclosed herein, is usually not more than about 50 mm. Therefore, the permanent magnet transducer according to the present invention may be used primarily for manual operation. Naturally, the permanent magnet transducer may also be used stationarily in a complex testing and inspection system.

One feature of the invention resides broadly in an electrodynamic permanent magnet transducer, consisting of a housing to be applied to workpiece surfaces to be inspected, whereby inside the housing is a permanent magnet which is magnetized perpendicular to the workpiece surface, and a transducer coil, which is designed as a spiral flat coil and is located in the vicinity of the workpiece surface to be inspected, and is connected to electrical connections which are also located on the housing, characterized by the combination of the following features: that the housing 2 consists of a soft magnetic material and is provided with an opening 4 facing the workpiece surface 21, that inside the housing, a hollow cylindrical body 3 consisting of non-magnetic material is fitted, and the permanent magnet 6 is located inside the hollow cylindrical body 3, that the pole surface facing away from the workpiece surface is in magnetically conducting contact with the corresponding inside wall of the housing, that there is a support body which holds the transducer coil 9 flush with the housing 2 in the opening 4, and inside the support body is fitted a soft magnetic concentrator body 7, that on the side 19 of the support body 5 facing the workpiece surface, there is a second spiral transducer coil 10, that the second transducer coil 10 circularly surrounds the first transducer coil 9, and the inside diameter of the second transducer coil 10 is larger than the outside diameter of the first transducer coil 9, that above the closed end of the soft magnetic housing 2 there is a connector box 1, which consists of a non-magnetic material.

Another feature of the invention resides broadly in an electrodynamic permanent magnet transducer characterized by the fact that the support body 5 consists of a non-magnetic material and has a recess 8 which tapers conically toward the workpiece surface, and that the concentrator body 7 has the same conicity and is located so that it fills up at least the conical portion of the recess 8.

A yet another feature of the invention resides broadly in an electrodynamic permanent magnet transducer characterized by the fact that the support body 5, on the side 19 facing the workpiece surface, has a first circular recess 12, and that a second circular recess 11 with a smaller diameter and greater depth is located inside the first recess 12.

A yet further feature of the invention resides broadly in an electrodynamic permanent magnet transducer characterized by the fact that the transducer coils 9, 10 are jointly fastened on one of the sides of s circular disc 18, that the disc 18 is fitted into the first recess 12 of the support body 5 so that the transducer coils 9, 10 project into the second recess 11 and the remaining space in the second recess 11 is filled with a plastic compound.

A still yet further feature of the invention resides broadly in an electrodynamic permanent magnet transducer characterized by the fact that the disc 18 consists of an abrasion-resistant plastic.

A yet still further feature of the invention resides broadly in an electrodynamic permanent magnet transducer characterized by the fact that there are holes 13, 13' leading laterally through the connector box 1 into the recess 14, and that the electrical connections consist of coaxial cable connections at least partly countersunk in the holes 13, 13'.

Several U.S. patents describe various types of electromagnetic acoustical transducers and/or components therefor. Various components found in those patents, such as transducer coils and permanent magnets, may be utilized in the embodiments of the present invention. Additionally, examples of methods and/or techniques for using electromagnetic acoustical transducers, which methods and/or techniques may be utilized with the embodiments of the present invention, may be found in those patents. The patents are: U.S. Pat. No. 4,777,824, entitled "Electromagnetic Acoustic Transducer", which issued on Oct. 18, 1988; U.S. Pat. No. 4,523,473, "Magneto-elastic Material Defect Detector", Jun. 18, 1985; U.S. Pat. No. 4,449,411, "Magnetic and Ultrasonic Objects Testing Apparatus", May 22, 1984; U.S. Pat. No. 4,434,663, "Electromagnetic Acoustic Transducer", Mar. 6, 1984; U.S. Pat. No. 4,420,978, "Method and Device for Transmitting and Receiving Electromagnetic Ultrasound", Dec. 20, 1983; U.S. Pat. No. 4,395,913, "Broadband Electromagnetic Acoustic Transducers", Aug. 2, 1983; U.S. Pat. No. 4,296,486, "Shielded Electromagnetic Acoustic Transducers", Oct. 20, 1981; and U.S. Pat. No. 4,102,207, "Electromagnetic Ultrasound Transducer", Jul. 25, 1978.

All, or substantially all, of the components and methods of the various embodiments may be used with at least one embodiment or all of the embodiments, if any, described herein.

All of the patents, patent applications and publications recited herein, if any, are hereby incorporated by reference as if set forth in their entirety herein.

The details in the patents, patent applications and publications may be considered to be incorporable, at applicant's option, into the claims during prosecution as further limitations in the claims to patentably distinguish any amended claims from any applied prior art.

The invention as described hereinabove in the context of the preferred embodiments is not to be taken as limited to all of the provided details thereof, since modifications and variations thereof may be made without departing from the spirit and scope of the invention.

What is claimed is:

1. An electromagnetic transducer at least for detecting defects in a workpiece, said transducer comprising:
    an external housing;
    magnet means disposed within said housing;
    said magnet means having a first pole and a second pole, the first pole for being disposed substantially toward the workpiece;
    said magnet means being for producing a magnetic field, the magnetic field for being applied to the workpiece;
    coil means for inducing current in the workpiece, said coil means being configured for being disposed substantially adjacent the workpiece;
    the magnetic field from said magnet means and the current from said coil means for interacting with each other to generate sonic waves;
    the first pole of said magnet means being disposed substantially adjacent said coil means;
    the second pole of said magnet means being disposed substantially opposite the first pole of said magnet means;
    magnetic conducting means being in magnetically conducting contact with the second pole of said magnet means;
    said magnetic conducting means for being disposed to be in simultaneous magnetically conducting contact with the workpiece and the second pole of said magnet means to direct the magnetic field between the workpiece and the second pole of said magnet means;
    support means supporting said coil means;
    said support means being configured for being disposed substantially adjacent the workpiece;
    concentrator means for directing the magnetic field between the magnet means and the coil means; and
    said concentrator means being disposed substantially adjacent said support means.

2. The transducer according to claim 1, wherein at least a portion of said external housing comprises at least a portion of said magnetic conducting means.

3. The transducer according to claim 2, further comprising:
    electrical conductor connection means for receiving at least one electrical conductor; and
    said electrical conductor connection means comprising a nonmagnetic material.

4. The transducer according to claim 3, further comprising:
    said support means comprising a nonmagnetic material; and
    said support means supporting said concentrator means.

5. The transducer according to claim 4, wherein said transducer has a bottom portion being configured for being disposed substantially adjacent the workpiece, said transducer further comprising:
    said support means having a first recess and a second recess;
    each of said first and second recesses having at least one vertical, recessed dimension with respect to the bottom portion of said transducer and at least one horizontal, cross-sectional dimension;
    the at least one horizontal, cross-sectional dimension of said first recess being generally greater than the at least one horizontal, cross-sectional dimension of said second recess; and
    the at least one vertical, recessed dimension of said second recess being generally greater that the at least one vertical, recessed dimension of said first recess.

6. The transducer according to claim 5, further comprising:
    said coil means being disposed substantially within said second recess;
    disc means supporting said coil means;
    said disc means being disposed substantially within said first recess;
    said disc means comprising a substantially abrasion-resistant plastic material;
    said electrical conductor connection means comprising a box and at least one hole disposed substantially within said box;
    said box comprising a nonmagnetic material;
    said support means having a conical recess, said conical recess having a lower portion for being disposed substantially toward the workpiece and and upper portion substantially opposite the lower portion;
    each of the upper and lower portions of said conical recess having a diameter;
    the diameter of the lower portion of said conical recess being generally less than the diameter of the upper portion of said conical recess;
    said conical recess having a conicity;
    said concentrator means having a conicity generally equal to the conicity of said conical recess;
    said coil means comprising at least two transducer coils;
    one of said at least two transducer coils being for inducing the current in the workpiece for generating sonic waves;
    another of said at least two transducer coils being for receiving electromagnetic waves derived from sonic waves;
    nonmagnetic means at least partially surrounding said magnet means to substantially eliminate magnetic short circuiting of the magnetic field;
    said magnet means being for producing a static magnetic field, the static magnetic field for being applied to the workpiece;

said coil means being for inducing eddy currents in the workpiece;

said magnet means comprising a permanent magnet;

said permanent magnet for being magnetized in a direction substantially perpendicular to the workpiece surface;

said concentrator means comprising a soft magnetic material;

said magnetic conducting means comprising a soft magnetic material;

each of said first recess and second recess of said support means having a substantially circular shape;

said second recess being coaxially disposed within said first recess;

said second recess being filled with a plastic compound;

said transducer comprising a substantially cylindrical shape;

said nonmagnetic means comprising a substantially cylindrical shape;

said box comprising a recess disposed within said box;

said box having an external surface;

said at least one hole of said box being disposed between said external surface and said recess of said box;

said recess comprising a circular hole and an auxiliary opening superimposed on said circular hole;

said auxiliary opening having a shape comprising: first and second arcs;

each of said first and second arcs having a center and a radius;

the radius of said first arc being generally equal to the radius of said second arc;

each of said first and second semicircular arcs having a first endpoint and a second endpoint;

a line connecting said first endpoint of said first arc and said first endpoint of said second arc; and said second endpoint of each of said first and second arcs intersecting said circular hole;

said auxiliary opening being superimposed on said circular hole in the manner of a secant;

each of said at least one hole of said box intersecting said auxiliary opening at a substantially transverse angle;

said recess of said box for receiving electrical conducting means;

said nonmagnetic means comprising an aluminum material;

said magnet means comprising a substantially cylindrical shape;

said magnetic conducting means comprising a substantially cylindrical shape;

said magnetic conducting means comprising an upper portion being in magnetically conducting contact with the second pole of said magnet means;

the upper portion of said magnetic conducting means comprising a plurality of holes being disposed therethrough, said holes being configured for receiving electrical conducting means;

said nonmagnetic means having a plurality of holes disposed therethrough, said holes being configured for receiving electrical conducting means;

said support means having a plurality of holes disposed therethrough, said holes being configured for receiving electrical conducting means;

at least two of said holes of said support means being aligned with at least two of said holes of said nonmagnetic means and at least two of said holes of the upper portion of said magnetic conducting means to form at least two passages between the upper portion of said magnetic conducting means and said support means;

said coil means for being connected to electrical conducting means;

the at least two passage being configured for guiding electrical conducting means from said recess of said box to said coil means;

each of said box, said magnetic conducting means, said nonmagnetic means and said support means having a common central axis;

two of the at least two passages being offset from each other by an angle of about 90 degrees with respect to the common central axis; and said circular hole of said recess of said box being disposed eccentrically with respect to the common central axis.

7. An electromagnetic transducer at least for detecting defects in a workpiece, said transducer comprising:

an external housing;

magnet means disposed within said housing;

said magnet means having a fist pole and a second pole, the first pole for being disposed substantially toward the workpiece;

said magnet means being for producing a magnetic field, the magnetic field for being applied to the workpiece;

coil means for inducing current in the workpiece, said coil means being configured for being disposed substantially adjacent the workpiece;

the magnetic field from said magnet means and the current from said coil means for interacting with each other to generate sonic waves;

the first pole of said magnet means being disposed substantially adjacent said coil means;

the second pole of said magnet means being disposed substantially opposite the first pole of said magnet means;

said coil means comprising at least two transducer coils;

one of said at least two transducer coils being for inducing the current in the workpiece for generating sonic waves;

another of said at least two transducer coils being for receiving electromagnetic waves derived from sonic waves;

support means supporting said coil means;

said support means being configured for being disposed substantially adjacent the workpiece;

concentrator means for directing the magnetic field between the magnet means and the coil means; and said concentrator means being disposed substantially adjacent said support means.

8. The transducer according to claim 7, wherein one of said at least two transducer coils substantially surrounds at least another of said at least two transducer coils.

9. The transducer according to claim 8, further comprising:

electrical conductor connection means for receiving at least one electrical conductor; and said electrical conductor connection means comprising a nonmagnetic material.

10. The transducer according to claim 9, further comprising:
said support means comprising a nonmagnetic material; and
said support means supporting said concentrator means.

11. The transducer according to claim 10, wherein said transducer has a bottom portion being configured for being disposed substantially adjacent the workpiece, said transducer further comprising:
said support means having a first recess and a second recess;
each of said first and second recesses having at least one vertical, recessed dimension with respect to the bottom portion of said transducer and at least one horizontal, cross-sectional dimension;
the at least one horizontal, cross-sectional dimension of said first recess being generally greater than the at least one horizontal, cross-sectional dimension of said second recess; and
the at least one vertical, recessed dimension of said second recess being generally greater that the at least one vertical, recessed dimension of said first recess.

12. The transducer according to claim 11, further comprising:
said coil means being disposed substantially within said second recess;
disc means supporting said coil means;
said disc means being disposed substantially within said first recess;
said disc means comprising a substantially abrasion-resistant plastic material;
said electrical conductor connection means comprising a box and at least one hole disposed substantially within said box;
said box comprising a nonmagnetic material;
said support means having a conical recess, said conical recess having a lower portion for being disposed substantially toward the workpiece and and upper portion substantially opposite the lower portion;
each of the upper and lower portions of said conical recess having a diameter;
the diameter of the lower portion of said conical recess being generally less than the diameter of the upper portion of said conical recess;
said conical recess having a conicity;
said concentrator means having a conicity generally equal to the conicity of said conical recess;
magnetic conducting means being in magnetically conducting contact with the second pole of said magnet means;
said magnetic conducting means for being disposed to be in simultaneous magnetically conducting contact with the workpiece and the second pole of said magnet means to direct the magnetic field between the workpiece and the second pole of said magnet means;
nonmagnetic means at least partially surrounding said magnet means to substantially eliminate magnetic short circuiting of the magnetic field;
said magnet means being for producing a static magnetic field, the static magnetic field for being applied to the workpiece;
said coil means being for inducing eddy currents in the workpiece;
said magnet means comprising a permanent magnet;
said permanent magnet for being magnetized in a direction substantially perpendicular to the workpiece surface;
said concentrator means comprising a soft magnetic material;
said magnetic conducting means comprising a soft magnetic material;
each of said first recess and second recess of said support means having a substantially circular shape;
said second recess being coaxially disposed within said first recess;
said second recess being filled with a plastic compound;
said transducer comprising a substantially cylindrical shape;
said nonmagnetic means comprising a substantially cylindrical shape;
said box comprising a recess disposed within said box;
said box having an external surface;
said at least one hole of said box being disposed between said external surface and said recess of said box;
said recess comprising a circular hole and an auxiliary opening superimposed on said circular hole;
said auxiliary opening having a shape comprising:
first and second arcs;
each of said first and second arcs having a center and a radius;
the radius of said first arc being generally equal to the radius of said second arc;
each of said first and second semicircular arcs having a first endpoint and a second endpoint;
a line connecting said first endpoint of said first arc and said first endpoint of said second arc; and
said second endpoint of each of said first and second arcs intersecting said circular hole;
said auxiliary opening being superimposed on said circular hole in the manner of a secant;
each of said at least one hole of said box intersecting said auxiliary opening at a substantially transverse angle;
said recess of said box for receiving electrical conducting means;
said nonmagnetic means comprising an aluminum material;
said magnet means comprising a substantially cylindrical shape;
said magnetic conducting means comprising a substantially cylindrical shape;
said magnetic conducting means comprising an upper portion being in magnetically conducting contact with the second pole of said magnet means;
the upper portion of said magnetic conducting means comprising a plurality of holes being disposed therethrough, said holes being configured for receiving electrical conducting means;
said nonmagnetic means having a plurality of holes disposed therethrough, said holes being configured for receiving electrical conducting means;
said support means having a plurality of holes disposed therethrough, said holes being configured for receiving electrical conducting means;
at least two of said holes of said support means being aligned with at least two of said holes of said nonmagnetic means and at least two of said holes of the upper portion of said magnetic conducting means to form at least two passages between the upper portion of said magnetic conducting means and said support means;

said coil means for being connected to electrical conducting means;

the at least two passages being configured for guiding electrical conducting means from said recess of said box to said coil means;

each of said box, said magnetic conducting means, said nonmagnetic means and said support means having a common central axis;

two of the at least two passages being offset from each other by an angle of about 90 degrees with respect to the common central axis; and said circular hole of said recess of said box being disposed eccentrically with respect to the common central axis.

13. An electromagnetic transducer at least for detecting defects in a workpiece, said transducer comprising:

an external housing;

magnet means disposed within said housing;

said magnet means having a first pole and a second pole, the first pole for being disposed substantially toward the workpiece;

said magnet means being for producing a magnetic field, the magnetic field for being applied to the workpiece;

coil means for inducing current in the workpiece, said coil means being configured for being disposed substantially adjacent the workpiece;

the magnetic field from said magnet means and the current from said coil means for interacting with each other to generate sonic waves;

the first pole of said magnet means being disposed substantially adjacent said coil means;

the second pole of said magnet means being disposed substantially opposite the first pole of said magnet means;

nonmagnetic means at least partially surrounding said magnet means to substantially eliminate magnetic short circuiting of the magnetic field;

support means supporting said coil means;

said support means being configured for being disposed substantially adjacent the workpiece;

concentrator means for directing the magnetic field between the magnetic means and the coil means; and said concentrator means being disposed substantially adjacent said support means.

14. The transducer according to claim 13, further comprising:

electrical conductor connection means for receiving at least one electrical conductor; and said electrical conductor connection means comprising a nonmagnetic material.

15. The transducer according to claim 14, further comprising:

said support means comprising a nonmagnetic material; and said support means supporting said concentrator means.

16. The transducer according to claim 15, wherein said transducer has a bottom portion being configured for being disposed substantially adjacent the workpiece, said transducer further comprising:

said support means having a first recess and a second recess;

each of said first and second recesses having at least one vertical, recessed dimension with respect to the bottom portion of said transducer and at least one horizontal, cross-sectional dimension;

the at least one horizontal, cross-sectional dimension of said first recess being generally greater than the at least one horizontal, cross-sectional dimension of said second recess; and the at least one vertical, recessed dimension of said second recess being generally greater that the at least one vertical, recessed dimension of said first recess.

17. The transducer according to claim 16, further comprising:

said coil means being disposed substantially within said second recess;

disc means supporting said coil means;

said disc means being disposed substantially within said first recess;

said disc means comprising a substantially abrasion-resistant plastic material;

said electrical conductor connection means comprising a box and at least one hole disposed substantially within said box;

said box comprising a nonmagnetic material;

said support means having a conical recess, said conical recess having a lower portion for being disposed substantially toward the workpiece and and upper portion substantially opposite the lower portion;

each of the upper and lower portions of said conical recess having a diameter;

the diameter of the lower portion of said conical recess being generally less than the diameter of the upper portion of said conical recess;

said conical recess having a conicity;

said concentrator means having a conicity generally equal to the conicity of said conical recess;

magnetic conducting means being in magnetically conducting contact with the second pole of said magnet means;

said magnetic conducting means for being disposed to be in simultaneous magnetically conducting contact with the workpiece and the second pole of said magnet means to direct the magnetic field between the workpiece and the second pole of said magnet means;

said coil means comprising at least two transducer coils;

one of said at least two transducer coils being for inducing the current in the workpiece for generating sonic waves;

another of said at least two transducer coils being for receiving electromagnetic waves derived from sonic waves;

said magnet means being for producing a static magnetic field, the static magnetic field for being applied to the workpiece;

said coil means being for inducing eddy currents in the workpiece;

said magnet means comprising a permanent magnet;

said permanent magnet for being magnetized in a direction substantially perpendicular to the workpiece surface;

said concentrator means comprising a soft magnetic material;

said magnetic conducting means comprising a soft magnetic material;

each of said first recess and second recess of said support means having a substantially circular shape;
said second recess being coaxially disposed within said first recess;
said second recess being filled with a plastic compound;
said transducer comprising a substantially cylindrical shape;
said nonmagnetic means comprising a substantially cylindrical shape;
said box comprising a recess disposed within said box;
said box having an external surface;
said at least one hole of said box being disposed between said external surface and said recess of said box;
said recess comprising a circular hole and an auxiliary opening superimposed on said circular hole;
said auxiliary opening having a shape comprising:
first and second arcs;
each of said first and second arcs having a center and a radius;
the radius of said first arc being generally equal to the radius of said second arc;
each of said first and second semicircular arcs having a first endpoint and a second endpoint;
a line connecting said first endpoint of said first arc and said first endpoint of said second arc; and
said second endpoint of each of said first and second arcs intersecting said circular hole;
said auxiliary opening being superimposed on said circular hole in the manner of a secant;
each of said at least one hole of said box intersecting said auxiliary opening at a substantially transverse angle;
said recess of said box for receiving electrical conducting means;
said nonmagnetic means comprising an aluminum material;
said magnet means comprising a substantially cylindrical shape;
said magnetic conducting means comprising a substantially cylindrical shape;
said magnetic conducting means comprising an upper portion being in magnetically conducting contact with the second pole of said magnet means;
the upper portion of said magnetic conducting means comprising a plurality of holes being disposed therethrough, said holes being configured for receiving electrical conducting means;
said nonmagnetic means having a plurality of holes disposed therethrough, said holes being configured for receiving electrical conducting means;
said support means having a plurality of holes disposed therethrough, said holes being configured for receiving electrical conducting means;
at least two of said holes of said support means being aligned with at least two of said holes of said nonmagnetic means and at least two of said holes of the upper portion of said magnetic conducting means to form at least two passages between the upper portion of said magnetic conducting means and said support means;
said coil means for being connected to electrical conducting means;
the at least two passages being configured for guiding electrical conducting means from said recess of said box to said coil means;
each of said box, said magnetic conducting means, said nonmagnetic means and said support means having a common central axis;
two of the at least two passages being offset from each other by an angle of about 90 degrees with respect to the common central axis; and
said circular hole of said recess of said box being disposed eccentrically with respect to the common central axis.

* * * * *